United States Patent [19]

Caspari

[11] 4,097,387

[45] Jun. 27, 1978

[54] OLEFIN-DIMERCAPTO-THIADIAZOLE COMPOSITIONS AND PROCESS

[75] Inventor: Gunter Caspari, Wheaton, Ill.

[73] Assignee: Standard Oil Company (Indiana), Chicago, Ill.

[21] Appl. No.: 720,266

[22] Filed: Sep. 3, 1976

[51] Int. Cl.² .......................... C10M 1/38; C10M 3/32
[52] U.S. Cl. ..................................... 252/47.5; 252/47; 260/302 D
[58] Field of Search .................. 260/302 SD; 252/47, 252/47.5

[56] References Cited

U.S. PATENT DOCUMENTS

| | | | |
|---|---|---|---|
| 2,719,125 | 9/1955 | Roberts | 252/47 X |
| 2,719,126 | 9/1955 | Fields | 252/47 |
| 2,736,729 | 2/1956 | Krzikalla et al. | 260/302 SD |
| 3,691,183 | 9/1972 | Thaler | 260/302 SD |
| 3,821,236 | 6/1974 | Ripple | 252/47 X |
| 3,840,549 | 10/1974 | Blaha et al. | 252/47 X |

Primary Examiner—Allen B. Curtis
Attorney, Agent, or Firm—Mark J. DiPietro; Arthur G. Gilkes; William T. McClain

[57] ABSTRACT

Disclosed are a composition of matter, a process for making said composition, and a lubricating oil composition having improved anti-wear properties containing an effective amount of said composition of matter.

The composition of matter comprises olefin-dimercapto-thiadiazole compositions, especially an oil soluble reaction product of an olefin; lithium, sodium or potassium 2,5-dimercapto-1,3,4-thiadiazole or mixtures thereof; and a member selected from the group consisting of $S_2Cl_2$, $SCl_2$, $S_2Br_2$, $SBr_2$, R-S-Cl, R-S-Br, and mixtures thereof, wherein R comprises $C_1$–$C_{100}$ hydrocarbyl or bromo, chloro or hydroxy substituted hydrocarbyl.

Some of these compositions can be represented as follows:

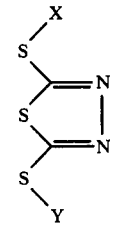

wherein X comprises $R_1$-SS-$R_2$, wherein $R_1$ comprises a $C_6$–$C_{100}$ hydrocarbyl or bromo, chloro or hydroxy substituted hydrocarbyl, and $R_2$ comprises $R_1$ or

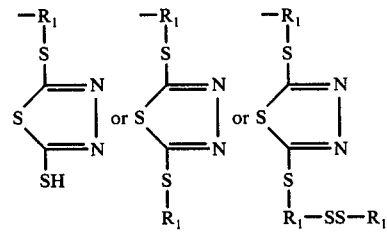

and wherein Y comprises H or X. Preferably $R_1$ comprises $C_6$–$C_{100}$ alkene or alkane, still more perferably, $C_6$–$C_{20}$ alkene or alkane. These compositions are effective wear inhibitors in lubricating oil.

The process for making oil soluble derivatives of 2,5-dimercapto-1,3,4-thiadiazole comprises first reacting an olefin with a member selected from the group consisting of $S_2Cl_2$, $SCl_2$, $S_2Br_2$, $SBr_2$, R-S-Cl, R-S-Br, and mixtures thereof, to form a first reaction product; and then reacting said first reaction product with lithium, sodium or potassium 2,5-dimercapto-1,3,4-thiadiazole or mixtures thereof.

50 Claims, No Drawings

OLEFIN-DIMERCAPTO-THIADIAZOLE COMPOSITIONS AND PROCESS

BACKGROUND

This invention relates to compositions of matter, a process for making said compositions of matter, and lubricating oils containing said compositions of matter. More specifically it relates to oil compositions having improved anti-wear properties and also other beneficial properties.

It is well known that various additives can be added to lubricating oils in order to improve various oil properties and to make a more satisfactory lubricant. Anti-wear agents are intended to decrease wear of machine parts. Wear inhibitors for incorporation in moter oils and industrial oils are finding greater use as a result of greater stress placed on moving parts in high performance engines. Numerous additives have been developed for use in such oil compositions to improve the lubricating characteristics thereof and thereby to lessen the wear of the moving parts.

It is an object of this invention to provide a new composition of matter and a process for making said composition.

It is an object of this invention to provide a lubricating oil composition having improved anti-wear properties.

It is further an object of this invention to provide a lubricating oil composition having multifunctional properties, such as extreme pressure; copper, lead and silver corrosion inhibition; and deactivation for sulfur and active sulfur compounds.

SUMMARY OF THE INVENTION

Disclosed are compositions of matter, a process for making said compositions, and a lubricating oil composition containing said compositions.

The composition comprises olefin-dimercapto-thiadiazole compositions, especially an oil soluble reaction product of an olefin; lithium, sodium or potassium 2,5-dimercapto-1,3,4-thiadiazole or mixtures thereof; and a member selected from the group consisting of $S_2Cl_2$, $SCl_2$, $S_2Br_2$, $SBr_2$, R—S—Cl, R—S—Br, and mixtures thereof, wherein R comprises $C_1$-$C_{100}$ hydrocarbyl or bromo, chloro or hydroxy substituted hydrocarbyl. Preferably R comprises a $C_1$-$C_{20}$ hydrocarbyl or bromo, chloro or hydroxy substituted hydrocarbyl.

Generally the olefin has a molecular weight of from about 80 to about 10,000, preferably from about 80 to about 500.

Preferred olefins are alpha-olefins, especially $C_6$-$C_{20}$ alpha-olefins. The preferred sulfur compound is $S_2Cl_2$.

Some of the disclosed compositions can be represented as follows:

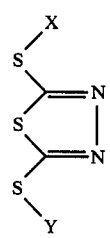

wherein X comprises $R_1$—SS—$R_2$, wherein $R_1$ comprises a $C_6$-$C_{100}$ hydrocarbyl or bromo, chloro or hydroxy substituted hydrocarbyl, and $R_2$ comprises $R_1$ or

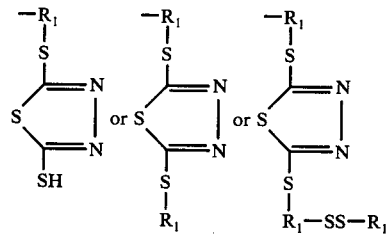

and wherein Y comprises H or X. Preferably $R_1$ comprises $C_6$-$C_{100}$ alkene or alkane, still more preferably, $C_6$-$C_{20}$ alkene or alkane. Some of these additives can be made by various other methods. These compositions are effective wear inhibitors in lubricating oil.

Generally the molar ratio of sulfur compound to thiadiazole to olefin is about 0.1–10:0.1–10:1, preferably about 0.3–1:2–4:1, and still more preferably 0.4–0.6-:2–4:1.

A process for making these oil soluble derivatives of 2,5-dimercapto-1,3,4-thiadiazole comprises first reacting an olefin with a member selected from the group consisting of $S_2Cl_2$, $SCl_2$, $S_2Br_2$, $SBr_2$, R—S—Cl, R—S—Br, and mixtures thereof, to form a first reaction product; and then reacting said first reaction product with lithium, sodium or potassium 2,5-dimercapto-1,3,4-thiadidazole or mixtures thereof. Commonly the reaction is conducted in a solvent.

The lubricating oil composition having improved anti-wear properties comprises a major proportion of lubricating oil and an effective amount of an oil soluble additive, said additive comprising the oil soluble reaction product of an olefin, lithium, sodium or potassium 2,5-dimercapto-1,3,4-thiadiazole or mixtures thereof, and a member selected from the group consisting of $S_2Cl_2$, $SCl_2$, $SBr_2$, $S_2Br_2$, R—S—Cl, R—S—Br, and mixtures thereof, wherein R comprises $C_1$-$C_{100}$ hydrocarbyl or bromo, chloro or hydroxy substituted hydrocarbyl.

A sulfur compound selected from the group consisting of $S_2Cl_2$, $SCl_2$, $S_2Br_2$, $SBr_2$, R—S—Cl, R—S—BR, and mixtures thereof is used. The hydrocarbyl R may be alkyl, olefinic or aromatic and may be chloro, bromo or hydroxy substituted. The character of R must be such that the final reaction product is oil soluble. Some of these sulfur compounds can be made by halogenation of hydrocarbyl mercaptans. For example, an alkyl mercaptan can be chlorinated with chlorine in a suitable solvent, such as carbon tetrachloride, at a temperature of about 0° C. Some of these sulfur compounds are commercially available.

Mono sodium 2,5-dimercapto-1,3,4-thiadiazole (Na-DMTD) is the preferred thiadiazole. Naturally, the mono sodium material will contain some amount of disodium thiadiazole. Mono sodium 2,5-dimercapto-1,3,4-thiadiazole can be made by reacting hydrazine hydrate with carbon disulfide in dilute sodium hydroxide. Commonly a small excess of sodium hydroxide is used to complete the reaction. This excess sodium hydroxide often results in some amount of disodium thiadiazole.

The olefin can be any olefin, cyclic or acyclic, from $C_4$ to olefins having a molecular weight of 100,000 or even higher. Polymeric olefins can be used. The term "polymer olefins" as used herein refers to amorphous copolymers derived from olefinically unsaturated monomers. Such olefin monomers include olefins of the general formula $RCH=CH_2$, in which R is an aliphatic or cycloaliphatic radical of from 1 to about 20 carbon atoms, for example, propene, isobutylene, butene-1, hexene-1, 4-methyl-1-pentene, decene-1, vinylidene norbornene, 5-methylene-2-norbornene, etc. Other olefin monomers having a plurality of double bonds may be used, in particular diolefins containing from about 4 to about 25 carbon atoms, e.g., 1,4-butadiene, 2,3-hexadiene, 1,4-pentadiene, 2-methyl-2,5-hexadiene, 1,7-octadiene, etc. These olefins often have number average molecular weights from about 80 to about 10,000, more preferably from about 80 to about 500. Of these polymers, a preferred group are polypropylene or butylene polymers. The olefin may be a copolymer, such as a ethylene-propylene-hexadiene terpolymer.

Preferred olefins are alpha-olefins, especially those containing from about 6 to about 20 carbon atoms. Some examples are hexene, heptene, octene, nonene, decene, dodecene, tetradecene, hexadecene, octadecene, eicosene, and the like. Often these olefins are commercially available as mixtures at somewhat lower cost. The olefin may be substituted by alkyl, aryl, alkylaryl, hydroxy, cyano, carboxylic acid, ester, halogen such as chlorine or bromine, or other groups so long as the substitution does not destroy the oil solubility of the final compound.

The lubricating oils in which the compositions of this invention are useful as additives and which comprise a major proportion of the lubricating oil compositions may be of synthetic, animal, vegetable, or mineral origin. Ordinarily mineral lubricating oils are preferred by reason of their availability, general excellence, and low cost. For certain applications, oils belonging to one of the other three groups may be preferred. For instance, synthetic polyester oils such as didodecyl adipate and di-2-ethylhexyl sebacate are often preferred as jet engine lubricants. Normally the lubricating oils preferred will be fluid oils, ranging in viscosity from about 40 Saybolt Universal seconds at 100° F. to about 200 Saybolt Universal seconds at 210° F. This invention contemplates also the presence of other additives in lubricating compositions. Such additives include, for example, viscosity index improving agents, pour point depressing agents, anti-foam agents, extreme pressure agents, rust-inhibiting agents, and oxidation and corrosion inhibiting agents.

The additive of this invention is generally added to lubricating oil in order to improve the anti-wear properties of said oil. Depending on the nature of the oil, the intended use and the desired improvement, different amounts of the additive are needed in order to be effective. Generally about 0.05 to about 5 weight percent, preferably from about 0.1 to about 2 weight percent, of the additive is used.

The olefin-sulfur compound, such as for example olefin-$S_2Cl_2$, reaction is usually carried out without solvent; however, the reaction may be conducted in inert solvents, such as paraffins, chlorinated hydrocarbons, ethers or others. The reaction temperature is commonly about 0° C. to about 200° C., preferably about 20° C. to about 60° C.

The olefin sulfur compound adduct — Na-DMTD reaction may be carried out in a suitable solvent. Solvents are preferred which dissolve Na-DMTD, such as water, alcohols, esters, ethers, ketones, or chlorinated solvents. The reaction temperature is commonly about 50° C. to about 200° C., preferably about 100° C.

A number of compounds were made first by preparation of an alpha-olefin—$S_2Cl_2$ adduct. One mole sulfur monochloride was added dropwise to two moles of α-olefins at room temperature. The temperature was not allowed to exceed 35° C. during addition. After addition, the temperature was raised to 65° C. and the reaction completed by stirring at this temperature for 3 hours. This adduct was then reacted with mono sodium 2,5-dimercapto-1,3,4-thiadiazole (Na-DMTD).

EXAMPLE 1

Iso Butylene—$S_2Cl_2$ + Na-DMTD

Isobutylene gas was fed through a subsurface gas sparger into 270 g $S_2Cl_2$ (2M) at a temperature of 45° C over a period of 8 hrs. The reaction flask, a 1 l three-necked flask, showed an increase in weight of 115 g.

124 g of the isobutylene-$S_2Cl_2$ adduct (0.5 m) were added dropwise at 50° C to 180 g monosodium DMTD dissolved in 200 ml water and 300 ml methanol. The reaction mixture was heated to reflux. The pH was continuously adjusted to neutral with aqueous sodium hydroxide. After three hours the reaction mixture was poured into 1 liter of ice-water. The oily layer was washed successively with 5% sodium hydroxide, 5% sulfuric acid, and twice with water. Residual water was removed by a stream of nitrogen at 80° C.

% found: C - 32.3,
H - 4.6
N - 9.5
S - 55.5
Cl - 0.2

EXAMPLE 2

1-Hexene — $S_2Cl_2$ — Na-DMTD 67.5 g $S_2Cl_2$ (0.5 m) were added dropwise at 35° C to 84 g hexene (1 m). After completed addition the reaction mixture was stirred for two hours at 50° C.

30 g of the hexene-$S_2Cl_2$ adduct (0.10 m) were added dropwise at 75° C under stirring to 44 g Na-DMTD (0.25 m) dissolved in 50 ml water and 150 ml isopropanol. The reaction mixture was refluxed for three hours and poured into 1 liter water, stirred for 10 minutes and cooled to 10° C. The oily layer was successively washed with 5% sodium hydroxide, 5% sulfuric acid, and twice with water. Residual water was removed by a stream of nitrogen at 80° C.

% found: C — 46.9; H — 6.4; N — 4.2; S — 34.3; Cl — 2.2

EXAMPLE 3

1-Octene — $S_2Cl_2$ — Na-DMTD 112 g octene (1 m) were reacted with 67.5 g $S_2Cl_2$ (0.5 m) as described in Example 2.

72 g of the octene-$S_2Cl_2$ adduct (0.2 m) were reacted with 88 g Na DMTD (0.5 m) in 100 ml water and 300 ml isopropanol as described in Example 2.

% found: N — 5.2; S — 32.5

EXAMPLE 4

$C_{11-14}$ α-olefin — $S_2Cl_2$ — 1 mole Na-DMTD 200 g $C_{11-14}$ α-olefin (1.2 m) were reacted with 81 g $S_2Cl_2$ (0.6 m) as described in Example 2.

A mixture of 94 g $C_{11-14}$ α-olefin-$S_2Cl_2$ adduct (0.2 m) and 44 g Na DMTD (0.25 m) in 50 ml water and 200 ml methanol was heated to reflux for 3 hrs. Aqueous sodium hydroxide was added to adjust the pH to neutral. On cooling, two layers formed. The lower layer was washed successively with 5% sodium hydroxide, 5% sulfuric acid, and twice with a mixture of equal volumes of water and methanol. Blowing with nitrogen at 80° C removed water and methanol and yielded a dark, viscous oil.

% found: N — 4.2; S — 26.1

EXAMPLE 5

$C_{11-14}$ α-olefin-$S_2Cl_2$ mole Na-DMTD

A mixture of 94 g $C_{11-14}$ α-olefin-$S_2Cl_2$ adduct (0.2 m) and 88 g Na-DMTD (0.5 m) in 100 ml water and 300 ml methanol were reacted as described in Example 4.

% found: N — 5.5; S — 32.5

EXAMPLE 6

$C_{15-20}$ α-olefin -$S_2Cl_2$ — Na-DMTD

252 $C_{15-20}$ α-olefin (1 m) were reacted with 67.5 g $S_2Cl_2$ (0.5 m) as described in Example 2.

77.4 g (0.2 m) of the $C_{15-20}$α-olefin-$S_2Cl_2$ adduct and 44 g Na-DMTD (0.25 m) in 50 ml water and 200 ml methanol were reacted as described in Example 4.

% found: N — 3.8; S — 23.5

EXAMPLE 7

$C_{15-20}$α-olefin — $S_2Cl_2$ — 2Na-DMTD 77.4 g of the $C_{15-20}$α-olefin-$S_2Cl_2$ adduct (0.2 m) and 88 g Na-DMTD (0.5 m) in 100 ml water and 250 ml methanol were reacted as described in Example 4.

% found: N — 5.1; S — 27.9

The extreme pressure properties were assessed by the Falex Lubricant Tester (ASTM D3233). The test consists of pressing a rotating steel journal at 290 rpm against two stationery steel V-blocks immersed in the lubricant sample. Load is applied by an automatic loading ratchet and is increased to 500 lbs. The machine is allowed to run at this pressure for three minutes (break-in period). The load is then increased at a rate governed by the automatic ratchet until failure occurs.

Oil Formulation:
7% Ashless dispersant
5% VI improver
40% 5W oil
48% 10W oil

| Example | Additive | Conc. (wt.%) | Jaw Load at Failure (lbs) |
|---|---|---|---|
| — | No additive | — | 750 |
| 1 | 1-butylene-$S_2Cl_2$-DMTD | 0.5 | 2700 |
|   |   | 1.0 | 2500 |
| 2 | 1-hexene-$S_2Cl_2$-DMTD | 0.75 | 2700 |
|   |   | 1.50 | 2600 |
| 3 | 1-octene-$S_2Cl_2$-DMTD | 0.75 | 2550 |
|   |   | 1.50 | 2500 |
| 4 | $C_{11-14}$α-olefin-$S_2Cl_2$-DMTD | 0.75 | 2550 |
|   |   | 1.50 | 2650 |
| 5 | $C_{11-14}$α-olefin-$S_2Cl_2$-2DMTD | 0.75 | 3250 |
|   |   | 1.50 | 2600 |
| 6 | $C_{15-20}$α-olefin-$S_2Cl_2$-DMTD | 0.75 | 2450 |
|   |   | 1.50 | 2500 |
| 7 | $C_{15-20}$α-olefin-$S_2Cl_2$-2DMTD | 0.75 | 2850 |
|   |   | 1.50 | 2750 |

Copper corrosion properties were assessed by the ASTM-D130 test. In this test, a polished copper strip is immersed in a given quantity of sample and heated at a temperature for a time characteristic of the material being tested. At the end of this period the copper strip is removed, washed, and compared with the ASTM copper corrosion standards. Here the test conditions were 30 g decalin plus 1.3 ml of a solution of 100 ml $CHCl_3$ + 1 g precipitated sulfur. The test solution was heated with additive and test strip to 212° F. for 3 hours.

| Example | Additive | Conc (wt.%) | ASTM-D130 Rating |
|---|---|---|---|
|   | No additive | — | 4C |
| 1 | 1-butylene-$S_2Cl_2$-DMTD | 0.5 | 1B |
| 2 | 1-hexene-$S_2Cl_2$-DMTD | 0.5 | 1B |
| 3 | 1-octene-$S_2Cl_2$-DMTD | 0.5 | 1B |
| 4 | $C_{11-14}$α-olefin-$S_2Cl_2$-DMTD | 0.5 | 1A |
| 5 | $C_{11-14}$α-olefin-$S_2Cl_2$-2DMTD | 0.5 | 1A |
| 6 | $C_{15-20}$α-olefin-$S_2Cl_2$-DMTD | 0.5 | 1B |
| 7 | $C_{15-20}$α-olefin-$S_2Cl_2$-2DMTD | 0.5 | 1B |

The copper-lead corrosion test assesses the oxidation corrosion inhibition of lubricants. Copper and lead specimen are immersed in a tube containing 100 g test oil and subjected to oxidation at 325° F. and 30 cc air per minute for 20 hours. At the end of the test, the difference in weight before and after the test is measured.

Oil Formulation:
7% Ashless dispersant
5% VI improver
2% Hindered alkyl phenol

| Example | Additive | Conc. (wt.%) | ΔCu, mg | ΔPb, mg |
|---|---|---|---|---|
|   | No additive |   | −4.8 | −349 |
| 1 | 1-butylene-$S_2Cl_2$-DMTD | 0.5 | +0.8 | −124.8 |
| 4 | $C_{11-14}$ α-olefin-$S_2Cl_2$-DMTD | 0.5 | +0.1 | −209.3 |
| 5 | $C_{11-14}$ α-olefin-$S_2Cl_2$-2DMTD | 0.5 | +1.5 | −142.5 |
| 6 | $C_{15-20}$ α-olefin-$S_2Cl_2$-DMTD | 0.5 | +0.7 | −168.5 |
| 7 | $C_{15-20}$ α-olefin-$S_2Cl_2$-2DMTD | 0.5 | +1.3 | −140.3 |

The anti-wear properties of an oil formulaton were assessed by means of the Four-Ball test. The Four-Ball test is usually referred to as the "Shell Four-Ball Test", introduced by Boerlage, G. D., Engineering 136, 46–47 (1933). This method consists of an apparatus where a single ball rotates under variable load on a support formed by three similar balls locked together in an oil cup. The Four-Ball machine was run at 130° F. at a load of 30, 50, and 70 kg at a speed of 1800 rpm. The wear scar diameter on the balls was measured after 30 minutes.

Oil Formulation: 5W oil
Test Conditions: 1800 rpm; 130° F; 0.5 hr.

| Example | Additive | Conc. Wt. % | Wear Scar Diameter (mm) | | |
|---|---|---|---|---|---|
| | | | 30 kg | 50 kg | 70 kg |
| | No additive | | —>2 mm after 1 min. at 30 kg | | |
| 2 | 1-Hexene-$S_2Cl_2$-DMTD | 1 | 0.65 | 0.73 | 1.05 |
| 3 | 1-Octene-$S_2Cl_2$-DMTD | 1 | 0.69 | 0.80 | 1.10 |
| 4 | $C_{11-14}$α-olefin-$S_2Cl_2$-DMTD | 1 | 0.71 | 0.85 | 1.15 |
| 5 | $C_{11-14}$αolefin-$S_2Cl_2$-2DMTD | 1 | 0.66 | 0.90 | 1.12 |
| 6 | $C_{15-20}$α-olefin-$S_2Cl_2$-DMTD | 1 | 0.75 | 0.90 | 1.20 |
| 7 | $C_{15-20}$α-olefin-$S_2Cl_2$-2DMTD | 1 | 0.68 | 0.85 | 1.15 |

Silver anti-wear properties were measured by a silver Four-Ball Wear Test. The test is essentially a Four-Ball Wear Test, only that a steel ball rotates on three silver disks instead of on steel balls. The test was run at 600 rpm, 500° F for 0.5 hours.

Oil Formulation: 2% overbased calcium phenate in HX-40

| Example | Additive | Conc.(wt.%) | Wear Scar Diameter (mm) |
|---|---|---|---|
| | No additive | — | 4.02 |
| 2 | Hexene-$S_2Cl_2$-DMTD | 0.75 | 2.82 |
| 2 | Hexene-$S_2Cl_2$-DMTD | 1.50 | 1.92 |
| 5 | $C_{11-14}$α-olefin-$S_2Cl_2$-2DMTD | 0.75 | 2.87 |
| 5 | $C_{11-14}$α-olefin-$S_2Cl_2$-2DMTD | 1.50 | 2.42 |

I claim:

1. A lubricating oil composition having anti-wear properties comprising a major proportion of lubricating oil and an effective amount of an oil soluble additive, said additive comprising the oil soluble reaction product of an olefin; lithium, sodium or potassium 2,5-dimercapto-1,3,4-thiadiazole or mixtures thereof; and a sulfur compound selected from the group consisting of $S_2Cl_2$, $SCl_2$, $S_2Br_2$, $SBr_2$, R—S—Cl, R—S—Br, and mixtures thereof, wherein R comprises $C_1$–$C_{100}$ hydrocarbyl or bromo, chloro or hydroxy substituted hydrocarbyl and said additive comprises,

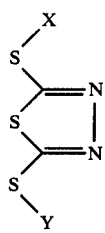

wherein X comprises $R_1$ — SS — $R_2$; $R_1$ comprises $C_6$–$C_{100}$ hydrocarbyl or bromo, chloro or hydroxy substituted hydrocarbyl, and $R_2$ comprises $R_1$ or

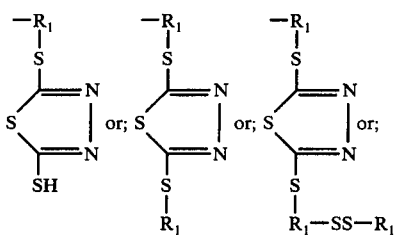

and Y comprises H or X.

2. The composition of claim 1 wherein the olefin has a molecular weight of from about 80 to about 10,000.

3. The composition of claim 2 wherein the olefin has a moleuclar weight of from about 80 to about 500.

4. The composition of claim 1 wherein the olefin comprises alfa-olefins.

5. The composition of claim 4 wherein the alfa-olefins comprise $C_6$–$C_{20}$ alfa-olefins.

6. The composition of claim 1 wherein R comprises $C_1$–$C_{20}$ hydrocarbyl or bromo, chloro or hydroxy substituted hydrocarbyl.

7. the composition of claim 1 wherein the molar ratio of sulfur compound to thiadiazole to olefin is about 0.1–10:0.1–10:1.

8. The composition of claim 7 wherein the molar ratio of sulfur compound to thiadiazole to olefin is about 0.3–1:2–4:1.

9. The composition of claim 8 wherein the molar ratio of sulfur compound to thiadiazole to olefin is about 0.4–0.6:2–4:1.

10. The composition of claim 5 wherein the alfa-olefins comprise isobutylene.

11. The composition of claim 5 wherein the alfa-olefins comprise 1-hexene.

12. The composition of claim 5 wherein the alfa-olefins comprise 1-octene.

13. The composition of claim 5 wherein the alfa-olefins comprise a mixture of $C_{11}$–$C_{14}$ alfa-olefins.

14. The composition of claim 5 wherein the alfa-olefins comprise a mixture of $C_{15}$–$C_{20}$ alfa-olefins.

15. The composition of claim 1 wherein the lubricating oil has a viscosity from about 40 Saybolt Universal Seconds at 100° F to about 200 Saybolt Universal Seconds at 210° F.

16. The composition of claim 1 wherein the additive is an oil soluble reaction product of an olefin, mono sodium 2,5-dimercapto-1,3,4-thiadiazole, and $S_2Cl_2$.

17. The composition of claim 1 wherein said additive is present at about 0.05 to about 5 weight percent.

18. The composition of claim 17 wherein said additive is present at about 0.1 to about 2 weight percent.

19. A composition comprising an oil soluble reaction product of an olefin; lithium; sodium or potassium 2,5-dimercapto-1,3,4-thiadiazole or mixtures thereof; and a member selected from the group consisting of $S_2Cl_2$, $SCl_2$, $S_2Br_2$, $SBr_2$, R—S—Cl, R—S—Br, and mixtures thereof, wherein R comprises $C_1$–$C_{100}$ hydrocarbyl or bromo, chloro or hydroxy substituted hydrocarbyl and said additive comprises,

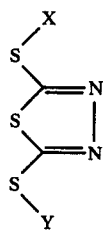

wherein X comprises $R_1$ — SS — $R_2$; $R_1$ comprises $C_6$–$C_{100}$ hydrocarbyl or bromo, chloro or hydroxy substituted hydrocarbyl, and $R_2$ comprises $R_1$ or

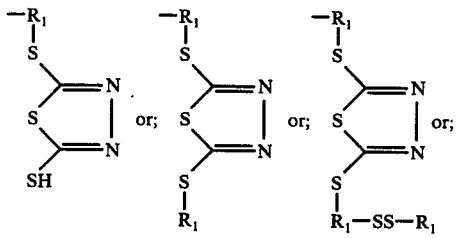

and Y comprises H or X.

20. The composition of claim 19 comprising a reaction product of an olefin, 2,5-dimercapto-1,3,4-thiadiazole.

21. The composition of claim 19 wherein the olefin has a molecular weight of from about 80 to about 10,000.

22. The composition of claim 21 wherein the olefin has a molecular weight of from about 80 to about 500.

23. The composition of claim 19 wherein the olefin comprises alfa-olefins.

24. The composition of claim 23 wherein the alfa-olefins comprise $C_6$–$C_{20}$ alfa-olefins.

25. The composition of claim 19 wherein R comprises $C_1$–$C_{20}$ hydrocarbyl or bromo, chloro or hydroxy substituted hydrocarbyl.

26. The composition of claim 24 wherein the alfa-olefins comprise isobutylene.

27. The composition of claim 24 wherein the alfa-olefins comprise 1-hexene.

28. The composition of claim 19 wherein the molar ratio of sulfur compound to thiadiazole to olefin is about 0.1–10:0.1–10:1.

29. The composition of claim 26 wherein the molar ratio of sulfur compound to thiadiazole to olefin is about 0.3–1:2–4:1.

30. The composition of claim 27 wherein the molar ratio of sulfur compound to thiadiazole to olefin is about 0.4–0.6:2–4:1.

31. The composition of claim 24 wherein the alfa-olefins comprise 1-octene.

32. The composition of claim 24 wherein the alfa-olefins comprise a mixture of $C_{11}$–$C_{14}$ alfa-olefins.

33. The composition of claim 24 wherein the alfa-olefins comprise a mixture of $C_{15}$–$C_{20}$ alfa-olefins.

34. A process for making oil soluble derivatives of 2,5-dimercapto-1,3,4-thiadiazole comprising first reacting an olefin with a sulfur compound selected from the group consisting of $S_2Cl_2$, $SCl_2$, $S_2Br_2$, $SBr_2$, R—S—Cl, R—S—Br, and mixtures thereof, to form a first reaction product; and then reacting said first reaction product with lithium, sodium or potassium 2,5-dimercapto-1,3,4-thiadiazole or mixtures thereof, wherein R comprises $C_1$–$C_{100}$ hydrocarbyl or bromo, chloro or hydroxy substituted hydrocarbyl.

35. The process of claim 34 wherein the reaction is conducted in a solvent.

36. The process of claim 34 wherein the molar ratio of sulfur compound to thiadiazole to olefin is about 0.1–10:0.1–10:1.

37. The process of claim 36 wherein the molar ratio of sulfur compound to thiadiazole to olefin is about 0.3–1:2–4:1.

38. The process of claim 37 wherein the molar ratio of sulfur compound to thiadiazole to olefin is about 0.4–0.6:2–4:1.

39. The process of claim 34 wherein the olefin and sulfur compound are reacted at a temperature from about 0° C. to about 200° C. and the first reaction product is reacted with the thiadiazole at a temperature from about 50° C. to about 200° C.

40. The process of claim 39 wherein the olefin and sulfur compound are reacted at a temperature from about 20° C. to about 60° C. and the first reaction product is reacted with the thiadiazole at a temperature of about 100° C.

41. The process of claim 34 wherein R comprises $C_1$–$C_{20}$ hydrocarbyl or bromo, chloro or hydroxy substituted hydrocarbyl.

42. The process of claim 34 wherein the olefin has a molecular weight of from about 80 to about 10,000.

43. The process of claim 42 wherein the olefin has a molecular weight of from about 80 to about 500.

44. The process of claim 43 wherein the olefin comprises alfa-olefins.

45. The process of claim 44 wherein the alfa-olefins comprise $C_6$–$C_{20}$ alfa-olefins.

46. The process of claim 44 wherein the alfa-olefins comprise isobutylene.

47. The process of claim 44 wherein the alfa-olefins comprise 1-hexene.

48. The process of claim 44 wherein the alfa-olefins comprise 1-octene.

49. The process of claim 44 wherein the alfa-olefins comprise a mixture of $C_{11}$–$C_{14}$ alfa-olefins.

50. The process of claim 44 wherein the alfa-olefins comprise a mixture of $C_{15}$–$C_{20}$ alfa-olefins.

* * * * *

UNITED STATES PATENT OFFICE
CERTIFICATE OF CORRECTION

Patent No. 4,097,387   Dated June 27, 1978

Inventor(s) Gunter Caspari

It is certified that error appears in the above-identified patent and that said Letters Patent are hereby corrected as shown below:

| Patent Office Column | Error Line | Error in Patent & Correction According to Specification |
|---|---|---|
| 1 | 17 | "moter" should be "motor" |
| 2 | 23 | "0.4-0.6-:2-4:1" should be "0.4-0.6:2-4:1" |
| 2 | 32 | "thiadidazole" should be "thiadiazole" |
| 3 | 66 | "aduct" should be "adduct" |
| 4 | 17 | "(2M)" should be "(2m)" |
| 4 | 60 | "Na DMTD" should be "Na -DMTD" |
| 5 | 2 | "Na DMTD" should be "Na -DMTD" |
| 5 | 14 | "$Cl_2$ mole" should be "$CL_2$ - 2 mole" |
| 5 | 23 | "252" should be "252g" |
| 5 | 33 | "$S_2cl_2$" should be "$S_2Cl_2$" |
| 5 | 39 | "stationery" should be "stationary" |

UNITED STATES PATENT OFFICE
CERTIFICATE OF CORRECTION

Patent No. 4,097,387          Dated June 27, 1978

Inventor(s) Gunter Caspari

It is certified that error appears in the above-identified patent and that said Letters Patent are hereby corrected as shown below:

| Patent Office Error | | Error in Patent & Correction |
| Column | Line | According to Specification |
|---|---|---|
| 6 | 19 | "copper corrosion" should be "copper strip corrosion" |
| 8 | 31 | "the" should be "The" |
| | | In claims 4-5, 10-14, 23-24, 26-27, 31-33, 44-50, "alpha-alefins" is misspelled as "alfa-olefins" |

Signed and Sealed this

Twenty-second Day of May 1979

[SEAL]

Attest:

RUTH C. MASON
Attesting Officer

DONALD W. BANNER
Commissioner of Patents and Trademarks